US012673150B2

(12) United States Patent
Klena et al.

(10) Patent No.: US 12,673,150 B2
(45) Date of Patent: Jul. 7, 2026

(54) MULTI-POSITION MODULAR CARBON DIOXIDE DETECTOR AND INDICATOR AND METHODS OF USE

(71) Applicants: James William Klena, Norfolk, VA (US); Christopher M. Sciortino, Virginia Beach, VA (US)

(72) Inventors: James William Klena, Norfolk, VA (US); Christopher M. Sciortino, Virginia Beach, VA (US)

( * ) Notice: Subject to any disclaimer, the term of this patent is extended or adjusted under 35 U.S.C. 154(b) by 301 days.

(21) Appl. No.: 18/431,099

(22) Filed: Feb. 2, 2024

(65) Prior Publication Data

US 2024/0424187 A1     Dec. 26, 2024

Related U.S. Application Data

(60) Provisional application No. 63/628,094, filed on Jun. 22, 2023.

(51) Int. Cl.
*A61M 39/12*     (2006.01)
*A61M 1/00*      (2006.01)
*G01N 31/22*     (2006.01)

(52) U.S. Cl.
CPC .............. *A61M 1/71* (2021.05); *A61M 39/12* (2013.01); *G01N 31/223* (2013.01); *A61M 2202/0014* (2013.01); *A61M 2202/0233* (2013.01); *A61M 2205/0227* (2013.01); *A61M 2205/15* (2013.01)

(58) Field of Classification Search
CPC ................... A61M 1/71; A61M 39/12; A61M 2202/0014; A61M 2205/0227; A61M 2205/15; G01N 31/223
See application file for complete search history.

(56) References Cited

U.S. PATENT DOCUMENTS

| | | | | |
|---|---|---|---|---|
| 8,246,752 B2 * | 8/2012 | Boyle, Jr. | .............. | A61B 90/70 |
| | | | | 134/8 |
| 10,842,920 B2 * | 11/2020 | Aho | ....................... | A61M 1/916 |
| 10,973,961 B2 * | 4/2021 | Eckardt | ................... | A61M 1/61 |
| 2009/0264833 A1 * | 10/2009 | Boyle, Jr. | .............. | A61B 90/70 |
| | | | | 604/257 |
| 2017/0368241 A1 * | 12/2017 | Aho | ........................ | A61M 1/90 |
| 2018/0050136 A1 * | 2/2018 | Eckardt | ................... | A61M 1/64 |
| 2019/0262515 A1 * | 8/2019 | Benharash | .............. | A61M 1/04 |
| 2024/0424187 A1 * | 12/2024 | Klena | ................... | G01N 31/223 |

FOREIGN PATENT DOCUMENTS

EP          3860671 B1 * 12/2024     .............. A61M 1/74

* cited by examiner

*Primary Examiner* — Guy K Townsend

(74) *Attorney, Agent, or Firm* — SLEMAN & LUND LLP

(57)                    ABSTRACT

In some examples, a method includes providing a leak detector having a body defining a viewing port, a sensor disposed within the viewing port, an inflow connection disposed on one side of the viewing port, and a vent disposed on an opposing side of the viewing port, wherein the inflow connection, the body and the vent define a lumen extending from the inflow connection through the viewing port and the vent, and coupling the leak detector to at least one of a chest tube and a chest tube drainage unit having a suction port.

19 Claims, 4 Drawing Sheets

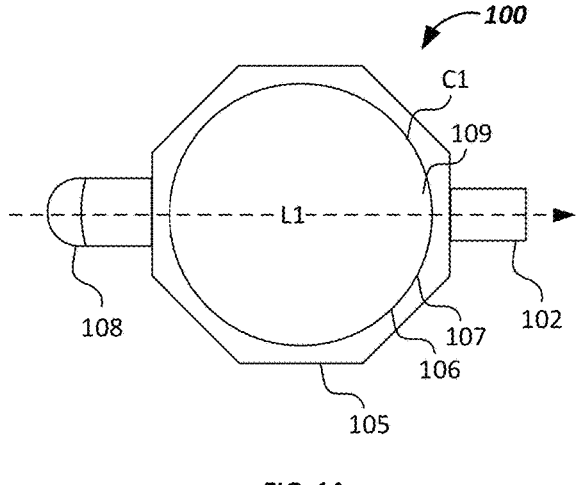
*FIG. 1A*
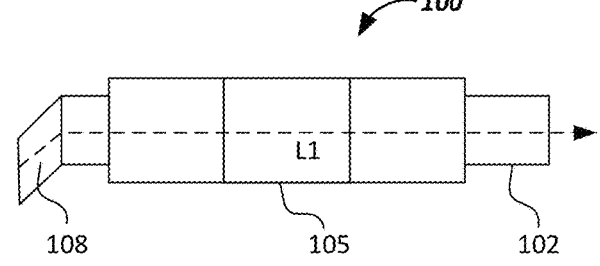
*FIG. 1B*
*FIG. 1C*

MULTI-POSITION MODULAR CARBON DIOXIDE DETECTOR AND INDICATOR AND METHODS OF USE

CROSS-REFERENCE TO RELATED APPLICATIONS

This application claims priority to U.S. Provisional Application Ser. No. 63/628,094, filed Jun. 22, 2023, entitled "SK Postoperative Pulmonary Carbon Dioxide Leak Detector," the contents of which are fully incorporated as if fully set forth herein.

FIELD OF THE DISCLOSURE

The present disclosure relates to carbon dioxide detectors useful in medical settings. More particularly the present disclosure relates to modular, multi-positionable carbon dioxide detectors and indicators.

BACKGROUND OF THE DISCLOSURE

Following pulmonary surgery, chest trauma or other lung injuries, tears in the lung parenchyma may vent into the pleural space instead of being expelled via the normal route of the bronchi and trachea leading to lung collapse and possibly death. This is referred to as an alveolar air leak and is treated by decompression of the pleural space with a tube (chest tube) and a collection device with a water seal preventing air from being sucked back into the pleural space with inspiration while venting the pleural space during expiration. A typical chest drainage system vents expiratory gas and collects blood and pleural fluid. The leak is vented through the system noted above until it resolves with subsequent removal of the chest tube. Contemporary management of an air leak involves surveillance of the collection system for the presence of expiratory gas bubbles exiting the patient and entering the venting system and seen in a leak meter on collection device. Establishing the presence of an air leak in this manner is imprecise and time consuming and can result in inappropriate chest tube removal with subsequent need for replacement. Ultimately this may result in increased patient discomfort and may extend the length of stay in the hospital. Digital collection devices have been developed to assist with air leak assessment but are expensive, and therefore not in widespread use. The vast majority of collection devices utilized for air leaks today are non-digital analog devices as described above.

SUMMARY OF THE DISCLOSURE

In some examples, a method includes providing a leak detector having a body defining a viewing port, a sensor disposed within the viewing port, an inflow connection disposed on one side of the viewing port, and a vent disposed on an opposing side of the viewing port, wherein the inflow connection, the body and the vent define a lumen extending from the inflow connection through the viewing port and the vent, and coupling the leak detector to at least one of a chest tube and a chest tube drainage unit having a suction port which also acts as an atmospheric vent when the system is not placed to suction.

In some examples, a leak detector includes a body defining a viewing port, a sensor disposed within the viewing port, an inflow connection disposed on one side of the viewing port, and a vent disposed on an opposing side of the viewing port, wherein the inflow connection, the body and the vent define a lumen extending from the inflow connection through the viewing port and the vent.

BRIEF DESCRIPTION OF THE DISCLOSURE

Various embodiments of the presently disclosed carbon dioxide detectors and indicators and associated systems are shown herein with reference to the drawings, wherein:

FIGS. 1A-1B illustrate schematic top and side views of a leakage detector and indicator;

FIG. 1C illustrates a schematic top view of the leakage detector and indicator of FIG. 1A after a color change of the sensor;

Figure 1D:
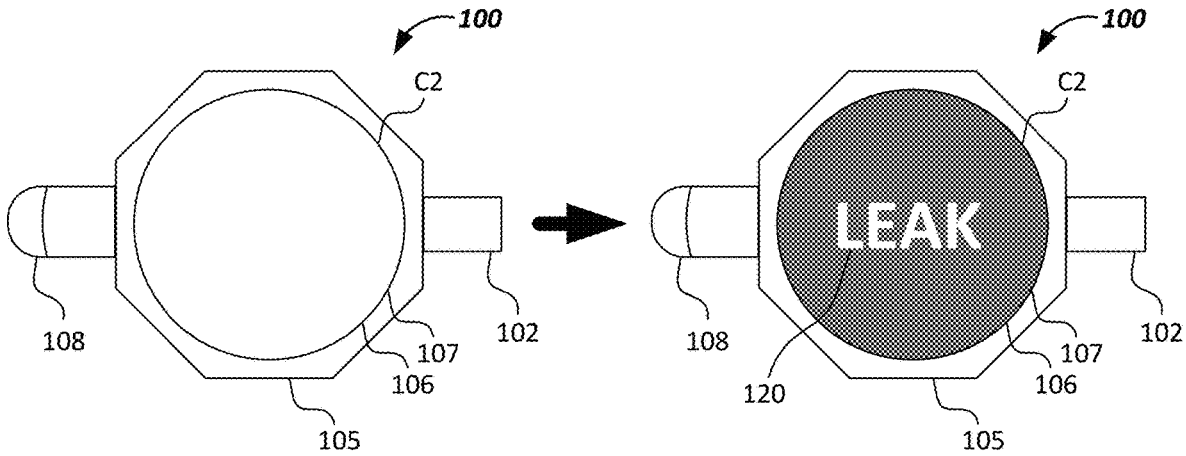
FIG. 1D illustrates a schematic top view of the leakage detector and indicator according to another embodiment.

Various embodiments of the present invention will now be described with reference to the appended drawings. It is to be appreciated that these drawings depict only some embodiments of the invention and are therefore not to be considered limiting of its scope.

DETAILED DESCRIPTION

Despite the various improvements that have been made to chest tubes, chest tube drainage units and their methods of use, conventional devices suffer from some shortcomings as described above.

There therefore is a need for further improvements to the devices, systems, and methods of detecting carbon dioxide. Among other advantages, the present disclosure may address one or more of these needs.

As used herein, the term "distal," when used in connection with a component, refers to the end of the component closest to the physician when the component when used with a patient, whereas the term "proximal," when used in connection with a component, refers to the end of the component farthest from the physician when used with a patient. Likewise, the terms "trailing" and "leading" are to be taken as relative to the operator (e.g., physician) of the assembly. "Trailing" is to be understood as relatively close to the operator, and "leading" is to be understood as relatively farther away from the operator.

The present disclosure relates to a single-use, disposable carbon dioxide detector that is modular and can be used in different positions to detect carbon dioxide during human expiration. In some examples, the detector may allow for instantaneous detection of carbon dioxide at levels of 50 ppm by revealing a color change in a colorimetric-based sensor connected to patient's existing chest tube and/or pleural evacuation device. Human expiratory gas contains 35,000-45,000 ppm $CO_2$ making the sensor exquisitely sensitive to $CO_2$ exposure. One purpose of the detector is to allow instantaneous recognition of the presence of carbon dioxide in the chest tube circuit so that determination of removal can be made promptly. Additionally, the device may be used in several positions, or as part of a kit. The correct use of the device may reduce length of stay for patients with chest tubes in place and reduce unnecessary pain in patients due to prolonged time with their chest tubes in place.

FIGS. 1A-1C illustrate one example of a carbon dioxide detector and indicator, referred to as detector 100. Detector 100 may generally include a vent 102 a body 105 having a colorimetric viewing port 106 and an inflow connection 108 (e.g., a suction port connection). A lumen LI may extend from inflow connection 108 through colorimetric viewing port 106 to vent 102. In some examples, inflow connection 108 is 8 mm in size and is angled as shown in FIG. 1B by between 30 and 60 degrees from the central axis of the device to allow visualization of the device when it is connected to a standard analog collection device. In some examples, inflow connection 108 is configured to mate with a suction or vent port of an analog collection system. Such a suction or vent port may be horizontally oriented and be approximately 8 mm in diameter and approximately 36 cm from the base of the collection device. In some examples, inflow connection 108 may be tapered, similar to a "Christmas Tree" type connection for universal compatibility with existing analog collection devices. Body 105 may be substantially octagonal as shown. This particular configuration of body 105 may resemble a stop sign and is designed to subliminally capture a physician or provider's attention. In some examples, viewing port 106 is circular as shown. It will be understood that the shape and/or size of the body 105 and viewing port 106 may be varied as desired. Viewing port 106 may be covered by a transparent plastic casing 109 (e.g., a flat or dome-shaped plastic covering) to protect the contents disposed therein. A sensor 107 is disposed within viewing port 106. In some examples, sensor 107 comprises an enclosed colorimetric capnography indication paper consisting of a filter paper treated with a solution of distilled water and 0.0065 M sodium carbonate with an additional equal volume of glycerol added; m-cresol purple added at 0.005% weight per volume of the final solution. The colorimetric capnography paper may have a first color C1 (e.g., purple) in the absence of carbon dioxide but may transition to a second color C2 (e.g., yellow) in the presence of carbon dioxide. In some examples chromophore consisting of a P4 grade filter paper that has been treated with ethanol and bis (4-pyridyl) dincopentoxyl-p-phenylenedivinylene (Np-P4VB). The chromophore may have a first color C1 (e.g., green) in the absence of carbon dioxide, but may transition to a second color C2 (e.g., orange) in the presence of carbon dioxide thus revealing the presence of an air leak or carbon dioxide (See, FIGS. 1A and 1C).

In some examples, sensor 107 may include a hidden message on the filter paper that only appears in the presence of carbon dioxide (FIG. 1D). The message (e.g., "LEAK" or "+"), for example, may be printed or disposed on the filter paper in a message color that is similar or close to the first color C1, and this message may become pronounced or appear to the physician when the sensor turns colors and provides a contrast with the hidden message 120. In some examples, the colorimetric substance or chromophore substance may be placed as a pattern on the filter paper and a message or symbol (e.g., + sign) may appear to indicate the presence of a leak. In some examples, two separate colorimetric substances may be disposed on the paper to achieve this.

Figure 2:
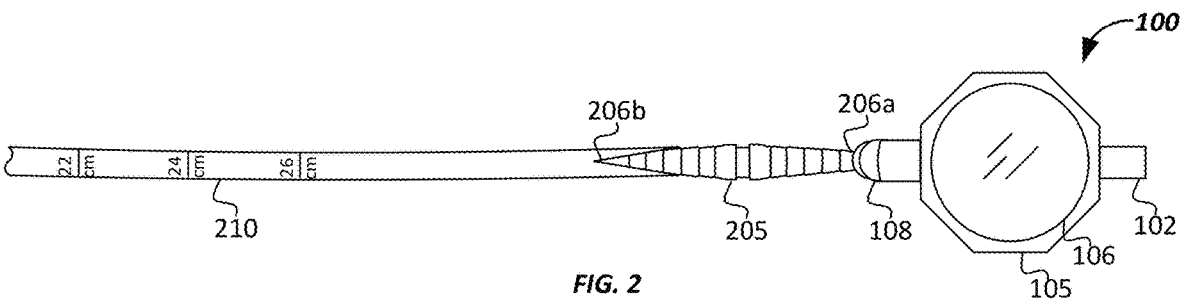
FIG. 2 illustrates a schematic top view of the leakage detector and indicator of FIG. 1A being coupled at a first position directly to a chest tube.

In one example, shown in FIG. 2, detector 100 is coupled directly to a patient's chest tube 210 via a mainstream connector 205. In this example, connection 205 is a simple straight double taper PP connector, often referred to as a "Christmas tree", used, for example, for connecting a suction source to suction waste collection systems, suction catheters, Yankauer suckers, suction probes and other suction devices. As shown, a first side 206a of connector 205 may be coupled or pushed into inflow connection 108 and the second side 206b may be coupled or pushed into a chest tube 210 to determine if there is leakage or carbon dioxide associated with using the chest tube.

Figure 3:
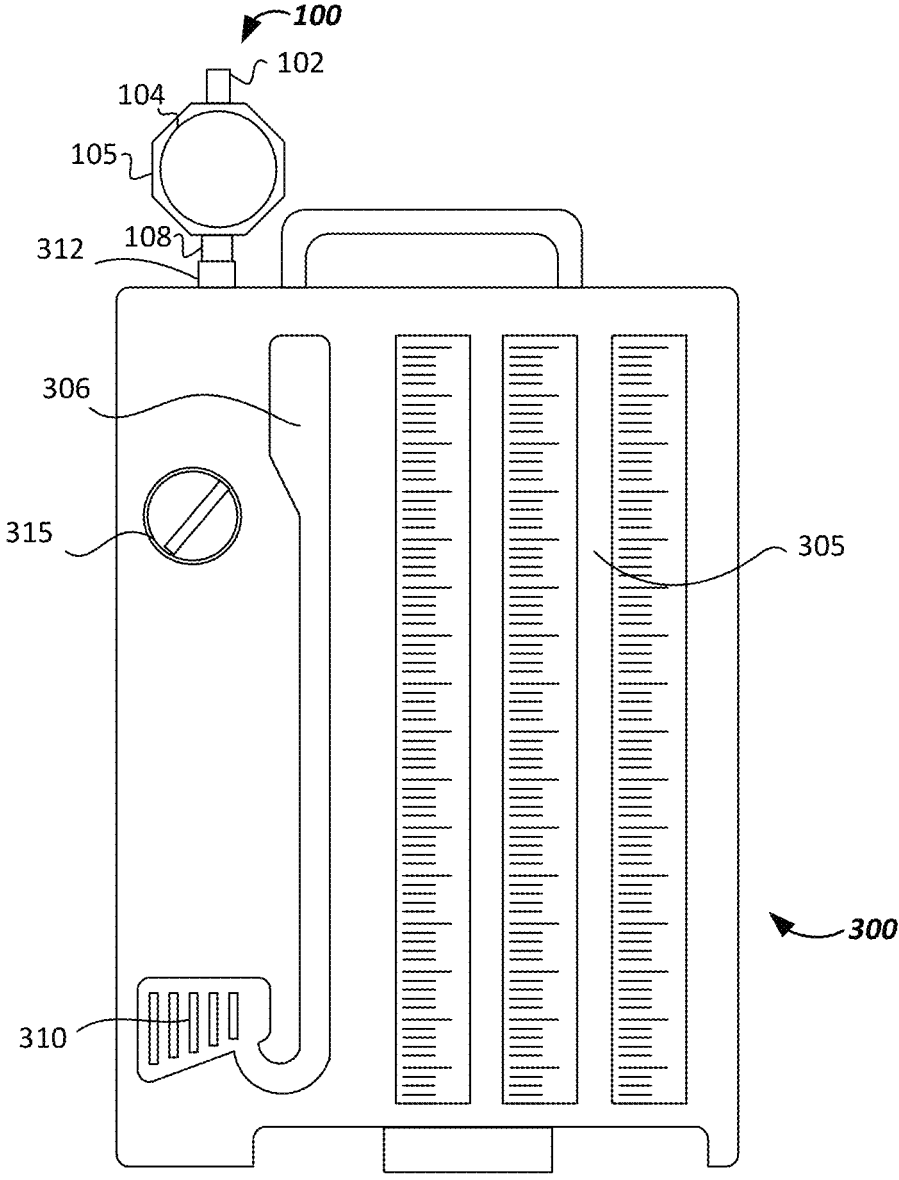
FIG. 3 illustrates a schematic front view of the leakage detector and indicator of FIG. 1A being coupled at a second position to a suction port of a chest tube drainage unit.

Turning to FIG. 3, before or after testing for leaks with the chest tube 210, detector 100 may also be used in conjunction with a chest tube drainage unit 300. For example, a physician may choose to use detector 100 with chest tube 210 or with chest tube drainage unit 300, or both. When using the detector 100 with multiple devices, the physician or user may choose the order in which the detector 100 is placed or select a sequence for diagnosis. Chest tube drainage unit 300 may be a sterile, disposable system that includes one or multiple chambers 305 to remove air or fluid and prevent return of the air or fluid back into the patient. A three-chamber 305 system is shown in FIG. 3. A chest tube may connect directly to the collection chamber, which collects drainage from the pleural cavity. Chest tube drainage unit 300 may include a water seal chamber 306 that functions as a one-way valve to allow air to exit the pleural cavity during exhalation but prevent it to from re-entering during inhalation due to the pressure in the chamber. Water-seal chamber 306 may be filled with a liquid (e.g., sterile water). In some examples, chest tube drainage unit 300 may include a dry suction regular knob 315 to adjust the amount of suction of the system. The chest tube drainage unit 300 may also include an analog air leak monitor 310. Chest tube drainage unit 300 may include a suction port 312 and inflow connection 108 of detector 100 may be coupled thereto. The use of detector 100 may provide an additional user-friendly, intuitive and easy-to-understand measure in addition the air leak monitor 310. In some examples, the detector 100 is placed at the top of the chest tube drainage unit 300 where it will be clearly visible to the healthcare provider. The length of inflow connection 108 may be chosen so that sensor 107 is clearly visible and spaced from the top of the chest tube drainage unit 300 by 1 cm-10 cm.

As noted, the same leak detector 100 may be used in multiple positions (e.g., initially at a first position with the chest tube as shown in FIG. 2, and then at a second position the site of the suction port of a chest tube drainage unit as shown in FIG. 3). That is, a physician may first couple detector 100 to the chest tube (e.g., via a double taper PP connector) and check for leaks, and then remove the detector and couple it to suction port 312 of the chest tube drainage unit 300. Of course, the user may choose to use the detector at only one position or may toggle between multiple positions as needed.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

What is claimed is:

1. A method comprising:
   providing a leak detector having a body defining a viewing port, a sensor disposed within the viewing port, an inflow connection disposed on one side of the viewing port, and a vent disposed on an opposing side of the viewing port, wherein the inflow connection, the body and the vent define a lumen extending from the inflow connection through the viewing port and the vent;
providing a symmetric double taper connector;
choosing a position for the leak detector, the position being selected from a first position on a chest tube and a second position on a chest tube drainage unit having a suction port;
coupling the inflow connection of the leak detector via the double taper connector to a first one of the first position on the chest tube and the second position on the suction port of the chest tube drainage unit;
decoupling the inflow connection of the leak detector from the first one of the first position on the chest tube and the second position on the suction port of the chest tube drainage unit; and
coupling the inflow connection of the leak detector via the double taper connector to a second one of the first position on the chest tube and the second position on the suction port of the chest tube drainage unit.

2. The method of claim 1, wherein coupling the leak detector to a first one comprises first coupling the leak detector to the chest tube.

3. The method of claim 2, wherein coupling the leak detector to the chest tube comprises mating the leak detector to a double taper PP connector.

4. The method of claim 3, further comprising the step of checking for carbon dioxide leakage as the leak detector is coupled to the chest tube.

5. The method of claim 4, wherein checking for carbon dioxide leakage comprises visually identifying a color of the sensor.

6. The method of claim 1, wherein coupling the leak detector to a first one comprises coupling the leak detector to the suction port of the chest tube drainage unit.

7. The method of claim 6, further comprising the step of checking for carbon dioxide leakage as the leak detector is coupled to the chest tube drainage unit.

8. The method of claim 7, wherein checking for carbon dioxide leakage comprises visually identifying a color of the sensor.

9. A leak detector comprising:
a body defining a viewing port;
a sensor disposed within the viewing port;

6 an inflow connection disposed on one side of the viewing port, the inflow connection being configured to mate with a symmetric double taper connector; and
a vent disposed on an opposing side of the viewing port;
wherein the inflow connection, the body and the vent define a lumen extending from the inflow connection through the viewing port and the vent.

10. A leak detector comprising:
a body defining a viewing port;
a sensor disposed within the viewing port;
an inflow connection disposed on one side of the viewing port; and
a vent disposed on an opposing side of the viewing port;
wherein the inflow connection, the body and the vent define a lumen extending from the inflow connection through the viewing port and the vent, and wherein the sensor comprises a filter paper treated with a solution of distilled water and 0.0065 M sodium carbonate with an additional equal volume of glycerol added; and m-cresol purple added at 0.005% weight per volume of the final solution.

11. The leak detector of claim 9, wherein the body is octagonal.

12. The leak detector of claim 11, wherein the viewing port is circular.

13. The leak detector of claim 9, wherein the sensor is configured to transition from a first color to a second color when exposed to carbon dioxide.

14. The leak detector of claim 13, wherein the first color is green and the second color is orange.

15. The leak detector of claim 9, wherein the inflow connection and the vent are aligned with one another.

16. The leak detector of claim 9, further comprising a plastic casing disposed over the viewing port.

17. A kit comprising:
a chest tube drainage unit having a suction port;
a chest tube; and
the leak detector of claim 1, the leak detector being selectively coupleable to at least one of the suction port and the chest tube.

18. The kit of claim 17, further comprising a connector for coupling the chest tube to the leak detector.

19. The kit of claim 18, wherein the connector is a double taper PP connector.

* * * * *